(12) United States Patent
Sovrano et al.

(10) Patent No.: US 7,704,359 B2
(45) Date of Patent: Apr. 27, 2010

(54) PRESSURIZED REFERENCE SYSTEMS AND PROCESS FOR THEIR PRODUCTION

(75) Inventors: Fabio Sovrano, Weesen (CH); Rolf Thrier, Tagelswangen (CH)

(73) Assignee: Hamilton Bonaduz AG, Bonaduz (CH)

( * ) Notice: Subject to any disclaimer, the term of this patent is extended or adjusted under 35 U.S.C. 154(b) by 1450 days.

(21) Appl. No.: 11/011,117

(22) Filed: Dec. 15, 2004

(65) Prior Publication Data
US 2005/0133369 A1 Jun. 23, 2005

(30) Foreign Application Priority Data
Dec. 17, 2003 (EP) .................... 03028997

(51) Int. Cl.
G01N 27/00 (2006.01)
G01N 27/26 (2006.01)
G01N 27/30 (2006.01)
G01N 27/403 (2006.01)

(52) U.S. Cl. .............. 204/435; 204/408; 204/414; 204/416

(58) Field of Classification Search .............. None
See application file for complete search history.

(56) References Cited

U.S. PATENT DOCUMENTS 6,468,408 B2  10/2002  Thrier et al.

2002/0189943 A1  12/2002  Fletcher et al.

FOREIGN PATENT DOCUMENTS

| DE | 37 02 501 A | 8/1987 |
|---|---|---|
| DE | 196 39 372 A1 | 4/1998 |
| DE | 100 53 979 A1 | 5/2002 |
| EP | 1 241 471 A1 | 3/2001 |
| GB | 2370646 A * | 7/2002 |
| JP | 8-145937 | 6/1996 |
| JP | 8-285811 | 11/1996 |
| WO | 02057765 A2 | 7/2002 |

* cited by examiner

*Primary Examiner*—Nam X Nguyen
*Assistant Examiner*—Kourtney R Salzman
(74) *Attorney, Agent, or Firm*—Rothwell, Figg, Ernst & Manbeck, P.C.

(57) ABSTRACT

The present application relates to a pressurized reference electrode and to a process for its production, said reference electrode comprising a chamber (11) which has a flowable reference electrolyte, and a portion of the wall of said chamber being formed from porous material (10) for contacting said reference electrode with a measuring medium, and said chamber being under overpressure, which is characterized in that the overpressure is generated in said reference electrode by introducing a gas or/and a liquid through said porous material of the wall in said chamber, or introducing said reference electrolyte into said chamber and closing said chamber under pressure.

13 Claims, 3 Drawing Sheets

PRESSURIZED REFERENCE SYSTEMS AND PROCESS FOR THEIR PRODUCTION

Figure 1:
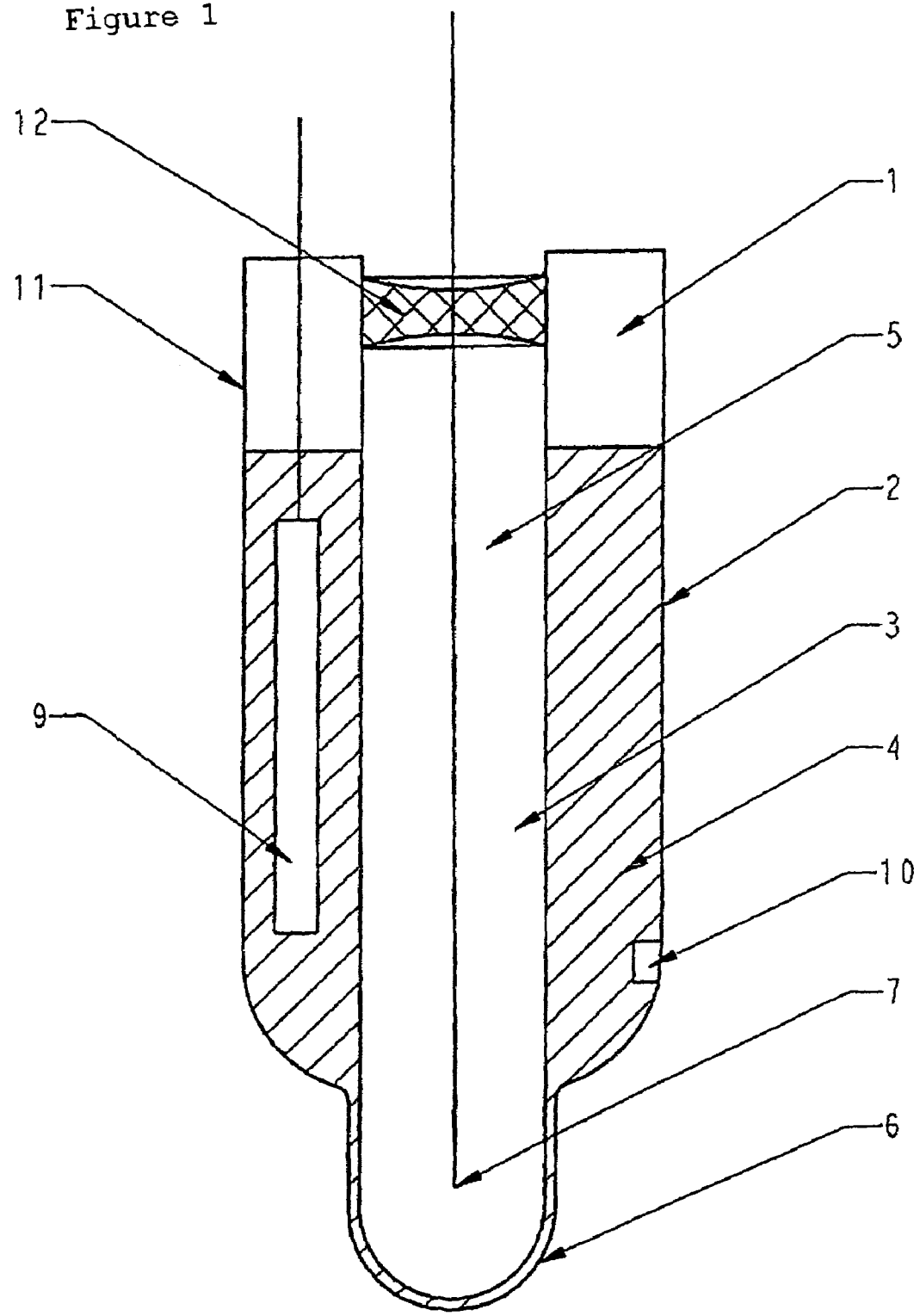

The present invention relates to a pressurized reference electrode and to a process for its production.

For the continuous monitoring of processes, potentiometric measuring cells and in particular pH measuring chains are often used. Such electrochemical measuring cells consist generally of a measuring electrode with ion-sensitive membrane and a reference electrode. The reference electrode may be formed separately or be connected to the measuring electrode via a bridge. The measuring electrode and reference electrode may also be present together in the form of single-rod measuring cells.

An essential prerequisite for exact and stable measurements in such processes is that the reference electrode or the reference element releases a constant half-cell voltage over a long time.

Numerous reference electrodes in various designs are known. They consist mostly of a discharge element in the form of an electrode of the second type, which is immersed into a reference electrolyte which determines the potential of the reference electrode. The reference electrolyte is in most cases a concentrated potassium chloride solution. The electrolytic contact between the discharge element and the measuring medium is made by a diaphragm disposed within the casing wall, for example a porous ceramic rod. Contamination of the diaphragm by the measuring medium or by the penetration of measuring medium into the reference electrolyte can result in incorrect potentials and thus distortion of the measuring results. The penetration of measuring medium can lead in this context to incorrect potentials in two ways. The first is by the dilution of the potential-determining electrolyte, which can lead to a decrease in electrolyte concentration in general and, in the case of an electrode of the 2nd type, to a decrease in the potential-determining halide concentration, and the second is as a result of penetrating electrode poisons, for example sulphides, which can alter the nature of the element of the 2nd type, for example by forming an Ag/AgS element, and thus its standard potential.

This is the case especially when the measuring medium, for example as a result of pressure increase or as a result of the static pressure of the measuring medium, has a higher pressure than the reference electrolyte at the location of the measuring chain. In this worst case, convective material currents into the reference system and accordingly particularly rapid poisoning and rapid changes in potential for the reference half-cell are to be expected.

In order to prevent this, the reference chamber is often pressurized, so that the internal pressure of the reference chamber is certain to be higher than the pressure of the measuring medium, in order at least to avoid contamination as a result of convective material currents. In addition, this achieves continuous flow of electrolyte out of the reference chamber during the measurement, which exhibits cleaning action for the diaphragm and is thus also capable of minimizing incorrect potentials as a result of contamination of the diaphragm with measuring medium. Finally, it should not be forgotten that an electrode with effluent electrolyte is obtained in this way, in which the circuit is completed by convectively transported ions and diffusion voltages at the diaphragm, which often constitute a further source of error in potentiometric measurements, can be minimized.

The pressurization has been effected in the past by various methods. The oldest known method is that of the pressure transducer, a pressurizable armature for the measuring chain, into which the electrodes are installed with an open reference chamber. The pressure applied here is transferred to the reference electrolyte owing to the open reference chamber and thus guarantees an overpressure relative to the measuring medium. A disadvantage of this method is the expensive pressure transducer (armature) needed for this purpose, into which the electrode has to be installed. In the case of unthickened electrolytes, an additional factor is that the electrodes have to be maintained frequently by replenishing the electrolyte.

Owing to these disadvantages, low-maintenance electrodes have been developed, in which the pressurized electrolyte has been thickened and thus flows out more slowly. Such electrodes, being low-maintenance electrodes, have been formed in such a way that it is no longer possible to replenish electrolyte.

DE 37 02 501 describes a pH measuring chain with pressurized reference electrode for microbiological processes. Disposed in the pH measuring chain above the reference electrolyte is a cavity in which there is a gas under pressure which is in contact with the reference electrolyte. The gas in the chamber of the reference chamber allows an internal pressure to be maintained which is greater than that of the measuring medium. A feed for the gas opens out in a cavity, which feed is attached in a gas-tight manner to the wall of the casing and can be sealed in a gas-tight manner. In a preferred embodiment, this feed is designed as a Pt capillary, which is sealed after the gas has been fed by clamping shut with a pincer.

DE 100 53 979 A1 describes pressurized reference chambers in which the pressure is generated in the reference chamber by strained springy elastic bodies. The elastic bodies used are either a metallic spring or else polymeric foam. The purpose of this design is, in contrast to DE 37 02 501, to provide a stable and reliable measuring chain in which any risk of injury is substantially avoided. In the event of fracture of the electrode, the strained springy body, in contrast to pressurized air, would only lose their strain slowly and prevent pieces of broken glass from flying around. A further advantage of this configuration, according to the applicant, is that, in contrast to DE 37 02 501, it is not necessary to incorporate an expensive Pt capillary into the glass of the reference chamber.

US 2002/0189943 A1 describes a pressurized electrolyte chamber in which the pressure is built up via a piston acting on the electrolyte. The piston may be driven by a spring fixed to the piston or by an external force.

A further way of ensuring electrolyte flow into the measuring medium is to connect a liquid-conveying pump between electrolyte chamber and measuring medium, whereas it has to be ensured here that the conveying rate is uniform and small in order to prevent excessively rapid outflow of electrolyte.

WO 02/057765 A2 mentions here the use of a micropump, as have been known for some time in microsystems technology. This method has all the advantages of a pressurized reference chamber, since outflow of reference electrolyte is also ensured here, but without keeping the actual reference electrolyte chamber under pressure.

EP 1241471 A1 describes a pressurized reference electrode, comprising a gel- or paste-like electrolyte which can be in contact with a measuring medium via a diaphragm, said reference electrode having a cavity which is sealed in a gas-tight manner and containing in the interior means for generating an overpressure. Suitable means are, for example, mechanical systems having a pressure spring or preferably chemical systems which release gas on activation. This generates a pressure in the reference electrode.

DE 19639372 A1 relates to an apparatus in which the electrolyte is placed under pressure by a piston system.

However, all previous methods are technically costly or associated with not insignificant costs. There is therefore still a need to find a process by which electrodes can be pressurized in a simple manner. It is therefore an object of the present invention to provide a pressurization process for reference electrodes which is simple to carry out, does not need any technically costly apparatus or auxiliary agents, and which enables inexpensive production of electrodes.

According to the invention, this object is achieved by a process for producing a reference electrode, said reference electrode comprising a chamber which has a flowable reference electrolyte, and a portion of the wall of said chamber being formed from porous material for contacting said reference electrode with a measuring medium, and said chamber being under overpressure, which is characterized in that the overpressure is generated in said reference electrode by introducing a gas or/and a liquid into said chamber through the porous material of the wall.

According to the invention, in contrast to the prior art, the pressure increase is brought about directly into a closed chamber of the reference electrode, in particular a closed reference chamber, through the porous diaphragm. In contrast to the pressurization methods of the prior art, this does not need any additional feed lines and it is possible, for example, to dispense with the use of an expensive Pt capillary. According to the invention, the pressure medium is instead introduced directly via a portion of the wall of the reference electrode.

Suitable reference electrolytes for a reference electrode are in principle any substances which exhibit a constant ion activity of the potential-determining species compared to the reference electrode and therefore lead to a constant potential at the reference electrode and which themselves exhibit electrolytic conductivity. The potential-determining species in Ag/AgCl electrodes of the second type is, for example, the chloride ion. The electrolyte used in accordance with the invention is flowable and can thus, after pressurization, overlay the diaphragm and thus prevent exit of the gas.

It is essential for the process of the present invention that a pressure is generated in the reference chamber by introducing a gas and/or a liquid penetrating through the diaphragm, through which the electrolyte is later in contact with the measuring medium, into the chamber. The pressurization is preferably effected by means of a gas through the porous electrode diaphragm, which may, for example, be a porous silica or zirconium oxide ceramic. While a pressurization is in principle also possible by pressurizing a liquid through the diaphragm into the reference chamber, it is often necessary in this procedure to pressurize with liquid at very high pressure and over a prolonged period, since the electrode diaphragms for liquids generally only have low permeability. Sufficiently high pressurization times and pressures do, however, allow very high pressures to be generated (hydraulically).

Advantageously, the pressurization is effected by means of a gas, for example by means of air. While it is possible using elastic, solid substances, as are used for pressurization in the prior art (cf. DE 10053979) only to set limited overpressures in the region of less than 2 bar, it is possible with the inventive method using compressed gases and, for example, pressurized air, to immediately achieve pressures of up to 10 bar of overpressure and more. In one embodiment, there is air in the electrolyte chamber (it is thus not free of air), which makes possible air pressurization and convection in the flowable electrolyte.

It is also particularly advantageous in the inventive method that the pressure is attained by pressing in a gas or/and a liquid through the diaphragm orifice which is present in any electrode in any case. Further, there is no need to provide any further feed orifices. It is also unnecessary to seal additional feed orifices, as are used in the prior art (cf. DE 10053979), after the pressurization.

A further advantage of the inventive pressurization process is that, owing to the high achievable reference pressure, effective protection can be provided against high process pressures.

A further significant advantage of the inventive pressurization method is the fact that the pressurization can be carried out in parallel, i.e. a multitude of reference electrodes can simultaneously be pressurized in one operation. An individual treatment of each individual reference electrode (for example the sealing of the Pt capillary with a pincer) is not required. Parallel pressurization can preferably be brought about by inserting or screwing a number of sealed reference chambers into a pressure vessel and subsequently simultaneously pressurizing them. Such a production in series is simple, robust and inexpensive.

According to the invention, a pressurized reference electrode is provided. This means in particular that the reference electrode comprises a chamber which is under overpressure. Overpressure refers to any pressure of $\geq 1.1$ bar, the chamber in particular having a pressure of $\geq 1.5$ bar, more preferably $\geq 2$ bar, in particular $\geq 3$ bar and more preferably $\geq 4$ bar. The pressure in the reference electrode may theoretically be arbitrarily high, but owing to technical considerations it is preferably a maximum of 20 bar, more preferably a maximum of 10 bar, in particular a maximum of 8 bar and most preferably a maximum of 6 bar.

The overpressure in the chamber, based on the intended use, may preferably be set in such a way that the pressure in the chamber is greater than the pressure of the measuring medium provided. The pressure in the chamber is preferably at least 1.1 times, more preferably at least 1.5 times, even more preferably at least 2 times and most preferably 4 times the pressure of the measuring medium.

According to the invention, the overpressure in the reference electrode is generated by a pressure medium, in particular by a gas or/and a liquid. On the basis of technical considerations, preferred gases are oxygen, nitrogen or/and air. However, it is also possible to provide the overpressure by introducing a liquid under pressure into the chamber of the reference electrode.

Particular preference is given to the porous material of the wall of the chamber having a higher permeability for the pressure medium than for the reference electrolyte, in particular at least twice, more preferably at least five times, in particular at least 50 times, even more preferably at least 100 times, more preferably at least 500 times and most preferably at least 1000 times, the permeability.

The pressure medium, in particular a liquid used as a pressure medium, preferably has a viscosity which is less than the viscosity of the reference electrolyte, in particular at least 100 times smaller and preferably at least 1000 times smaller than the viscosity of the reference electrolyte. The liquid preferably has a viscosity of at least 0.1 mPa·s, more preferably of at least 1 mPa·s and up to 5000 mPa·s, more preferably up to 1000 mPa·s, even more preferably of up to 500 mPa·s, in particular of up to 100 mPa·s and particularly preferably of up to 5 mPa·s. Particular preference is given to the pressure medium having a viscosity between 0.3 and 1 mPa·s. All viscosity data relate here to the dynamic viscosity at a measurement temperature of 25° C. The pressure-imparting liquids used may be any liquids, i.e. either inorganic or organic liquids. Particular preference is given to using water or a monoalcohol having from 1 to 10 carbon atoms. Further suitable liquids which can be used preferentially for pressure generation are aldehydes, ketones or organic compounds having from 1 to 10 carbon atoms, in particular linear, branched or cyclic compounds which may be saturated or unsaturated.

Preferred solvents include, for example, methanol, ethanol, 1-propanol, 2-propanol, 1-butanol, 2-butanol, 2-methyl-2-propanol, allyl alcohol, 1-pentanol, 2-pentanol, 3-pentanol, 1-heptanol, 2-heptanol, 3-heptanol, 4-heptanol, 1-octanol, 1-decanol, cyclohexanol, acetone, propanal, 2-butanone, dibutyl ether, acetonitrile, tetrahydrofuran, ethyl acetate, cyclopentane, cyclohexane, hexane, octane, o-xylene, m-xylene, p-xylene and others.

According to the invention, the pressure medium is introduced directly into the reference electrode through a portion of the wall of the chamber made of porous material. The portion of the wall is simultaneously formed for the contacting of the reference electrode with a measuring medium. The porous material has preferably pore sizes in the range of 0.1 to 10 μm (reported as the pore radius), more preferably of 1 to 5 μm (reported as the pore radius). Suitable materials for the porous material are, for example, zirconium oxides or silicates or other known porous "liquid junctions", for example porous sintered materials, wood and natural fibre materials, asbestos fibre bundles, fibre bundles, especially of celluloses or/and cotton wool, cotton wool bundles, twisted wires, for example twisted Pt wires, porous glasses, for example CPG ("controlled pore glass"), in particular Vycor, what is known as a "thirsty glass" (Dow Corning) which has controlled pores, glass sieves, porous silica gels or sintered porous polymers, such as Teflon or polypropylene. Preference is given to 0.1% to 50%, in particular 1% to 10%, of the wall of the chamber being made of porous material. Particular preference is given to the porous material consisting of a cylindrical rod (for example having a diameter of 0.5 mm to 1.5 mm, in particular 0.8 mm to 1.2 mm). The porous material has a pore radius of 0.5 μm to 1 μm and a porosity of 25% to 40%.

According to the invention, a different material flux is attained in the course of pressurization or pressure increase of the reference electrode by the pressurization medium, in particular a gas or a liquid, and in the course of use of the electrode, in which electrolyte flows out of the reference electrolyte in the opposite direction to the pressurization direction. In this context, it is appropriate to adjust pore size and permeability, and/or viscosity of reference electrolyte and pressurization medium, relative to one another such that firstly a sensibly short pressurization time, in particular of approx. 1 to 24 hours, can be maintained, and secondly a sufficiently long lifetime of the electrode is ensured, in the course of which the electrolyte should only flow out slowly (for example at an outflow rate of <5 ml/year). The flow rate through a porous body can be described by the equation of Hagen-Poiseuille. According to this, the flow rate $dV/dt$ is inversely proportional to the dynamic viscosity $\eta$ and directly proportional to the applied pressure differential $\Delta p$. This equation applies both in the course of pressurization and in the course of outflow. In the course of pressurization, a high pressure is typically applied, for example >10 bar, more preferably >20 bar and in particular at least 40 bar, in order to obtain a short pressurization time, where $\eta$=viscosity of the pressurization medium. In the course of outflow, $\Delta p$ represents the pressure differential between reference electrode and measuring medium and $\eta$=the viscosity of the resulting electrolyte (provided electrolyte mixed with pressurization medium).

According to the invention, the reference electrolyte running back into the porous cavity after the pressurization forms a type of non-return valve. In a further preferred embodiment, the electrolyte comprises polymers, in particular linear polymers, which are used to thicken the electrolyte and, owing to their molecular size, cannot pass through the pores of the porous diaphragms. In this case, the diaphragm forms a barrier to the polymer and/or the polymer contributes to an osmotic pressure, which is thus built up in the reference electrolyte chamber and counteracts outflow. For a pore radius of, for example, 0.4 to 0.6 μm, it has been found that a molecular size Mw=500 000 or greater is sufficient in order to achieve such a "blockage" of the diaphragm.

Since, in accordance with the invention, the overpressure is introduced via a portion of the wall, the reference electrode may be a system having a sealed casing, for example a sealed casing made of glass or plastic. The reference electrode therefore preferably does not have any further feed lines or orifices.

The chamber, which is to be pressurized, of the reference electrode has a reference electrolyte. The reference electrolyte is preferably a flowable and more preferably a flowable thickened electrolyte. When the pressure medium is used to increase the pressure, the reference electrolyte is displaced, so that the pressure medium can penetrate into the chamber. Owing to gravity, the reference electrolyte can flow back through the diaphragm orifice on completion of pressurization and thus prevent the pressure medium from exiting through the porous material of the diaphragm.

For the inventive type of pressurization, it is particularly advantageous when the reference electrolyte and the pressurization medium are selected such that the permeability of the two materials for the porous material differs so greatly that the reference electrolyte can flow back after the pressure buildup in the reference electrolyte chamber and blocks the porous material as a result of the overpressure in the chamber in a similar manner to a non-return valve, so that outflow of the pressure medium is prevented. The reference electrolyte preferably has a viscosity of at least 20 mPa·s, more preferably at least 40 mPa·s, more preferably at least 100 mPa·s and in particular at least 1000 mPa·s, and up to 20 Pa·s, in particular up to 5 Pa·s. Reference electrolytes having low flowability may be made flowable owing to their gravitation by elevated temperature in the course of pressurization, for example at least 50° C., and thus flow back through the porous diaphragm after the reference electrode has been filled with the pressure medium and seal it. The viscosity of the reference electrolyte is advantageously adjusted to the diaphragm porosity. Such an adaptation is preferably effected by adding a thickener to the reference electrolyte. Preference is given to using an aqueous KCl solution as the reference electrolyte itself. The thickeners used are preferably linear polymers, in particular hydrophilic linear polymers. Examples of such thickeners are linear polyacrylates and derivatives thereof, in particular water-soluble polyacrylates, cellulose derivatives, starch derivatives, dextroses, polyvinyl alcohols, poly-(N-vinylpyrrolidones), poly(2-vinylpyridines), polyethylene oxides, polyethylene glycols and derivatives thereof, such as polyethylene glycol monomethyl ethers, polyvinyl acetates, polymaleic acids, polyvinyl methyl ethers, gelatins, agar-agar and alginates. Particular preference is given to using polymers having chain lengths which can pass through the pores of the porous diaphragm only to a limited extent and more preferably not at all. The polymers used as thickeners therefore preferably have a molecular weight Mw of ≧100 000 Da, in particular ≧200 000 Da and more preferably of ≧500 000 Da. For a $ZrO_2$ diaphragm having a pore radius of 0.1 to 1 μm, in particular of 0.4 to 0.6 μm, penetration is fully prevented, for example for the pDMA thickener system, at a molecular weight Mw>500 000.

It is also possible to thicken the reference electrolyte with viscous organic solvents, in particular water-soluble viscous organic solvents, for instance di- or trialcohols (e.g. glycerol ethylene glycol or propylene glycol), polyols (e.g. hydroxy-terminal polyesters or/and polyethers, as find use as base construction materials in polyurethane preparation) or amines (e.g. triethanolamine). Such organic solvents preferably have a viscosity of >40 mPa·s. Further examples of organic solvents suitable as thickeners are cyclohexanol and diethanolamine.

A particularly preferred thickener is linear poly-dimethylacrylamide (cf. U.S. Pat. No. 6,468,408; pDMA). U.S. Pat. No. 6,468,408 describes solvent- and acid-resistant polymers which, owing to their resistance, can be used preferentially as reference materials. Polydimethyl-acrylamide has the additional advantage over conventional polyacrylamides that it is less toxic and does not contain any acrylamide. Especially in applications in the biological, pharmaceutical or foods sector, an acrylamide-free electrolyte is of particular interest. According to the invention, polydimethylacrylamide is used uncrosslinked and thus flowable (and not as a solid electrolyte). Such a flowable electrolyte also has the advantages which arise owing to the material, i.e. a good acid stability (non-hydrolysable), a high solvent stability (does not precipitate in alcohol) and non-toxicity (no acrylamide in the process).

Linear polydimethylacrylamide is thickening and flowable and has the advantage of being acrylamide-free and thus substantially less toxic. Polydimethylacrylamide has good hydrolysis stability and good acid and solvent compatibility, and is attacked only to a slight extent by bioactive substances and enzymes. This is especially significant when applicated in biological processes, since bacterial poisons are firstly undesired in these processes and the polymer secondly must not decompose as a result of the bacterial enzymes from these processes to give a low-viscosity or thinfluid electrolyte. The acid and solvent resistance has in particular advantages in measurements in the chemical field, in which many polymers are degraded by hydrolysis or can precipitate in organic solvents. Both likewise lead to the loss of the viscosity, needed for this application, of the electrolyte and thus to reduced electrode lifetime.

The invention further relates to a process for producing a reference electrode, said reference electrode comprising a chamber which has a reference electrolyte, and a portion of the wall of said chamber being formed from porous material for contacting said reference electrode with a measuring medium, and said chamber being under overpressure, said process being characterized in that said reference electrolyte is introduced into said chamber and said chamber is closed under pressure, while said reference electrolyte and said chamber are kept under pressure. It is also possible with this embodiment of the process according to the invention to pressurize a reference system without an additional feed being required for the pressurization. In this procedure, the chamber containing the reference electrolyte is completed while it is kept under pressure. The sealing of the chamber may be effected, for example, by sticking together or fusion. Especially in the case of cylindrical glass bodies, preference is given to fusion. One process step for the sealing of the chamber is effected by applying precisely the pressure externally which is finally to be contained in the chamber. Preference is therefore given to carrying out the last manufacturing step of sealing in a pressure chamber. While the chamber and preferably the entire reference electrode is then kept under pressure, the chamber comprising the reference electrolyte is sealed, for example adhesive-bonded or fused. A feed for the subsequent introduction of pressure into the reference electrode is not needed in this procedure either. Particular preference is given to closing concentric tubes, in particular glass tubes, by fusion or sticking after the electrolyte has been filled in, in the course of which the electrolyte and the entire chamber are kept under pressure by an external pressure source and the process of closure by fusion or sticking is effected under pressure.

The invention further provides a reference electrode which is obtainable by the above-described process and a measuring chain comprising such an electrode. The inventive reference electrode has in particular, with the exception of the section made of porous material, no orifice or feed. Such an additional orifice or feed, as described in the prior art, is not required in the reference electrode according to the invention. Orifice or feed also refers to a feed which has become sealed reversibly or irreversibly, through which it was possible to apply pressure and which had been sealed, for example by melting, after the pressurization. The inventive reference electrode is pressurized through the porous orifice which is always present and is still present even after the pressurization, while no further orifice is required for the pressurization itself. In contrast, electrodes according to the prior art have further orifices during the pressurization, through which the pressure is applied, in which case these orifices are then sealed only after the pressurization so that the pressure no longer escapes. Such further orifices, as are provided in the prior art, are, for example, PT capillaries, annular orifices which are fused only after the pressurization, or a septum.

The invention further relates to electrochemical measuring cells which comprise an inventive reference electrode. Preferred are, for example, reference systems which are used in amperometric sensors, in voltammetry or in batteries, for example in fuel cells, and have been pressurized in accordance with the invention. Preference is given to using reference electrodes pressurized in accordance with the invention in potentiometric measuring chains.

The invention is further illustrated by the appended figures and the examples which follow.

FIG. 1 shows an electrode with sealed reference chamber which comprises a thickened, flowable reference electrolyte and a porous diaphragm. The individual reference numbers denote:

| | |
|---|---|
| 1. | cavity for holding gas |
| 2. | outer chamber for holding the reference electrolyte |
| 3. | internal buffer |
| 4. | reference electrolyte |
| 5. | inner chamber for holding the internal buffer |
| 5. | ion-sensitive membrane |
| 7. | internal discharge system for the ion-sensitive membrane |
| 9. | reference electrode |
| 10. | porous material (diaphragm) |
| 11. | a chamber which has a flowable reference electrolyte |
| 12. | fused seal |

Figure 2:
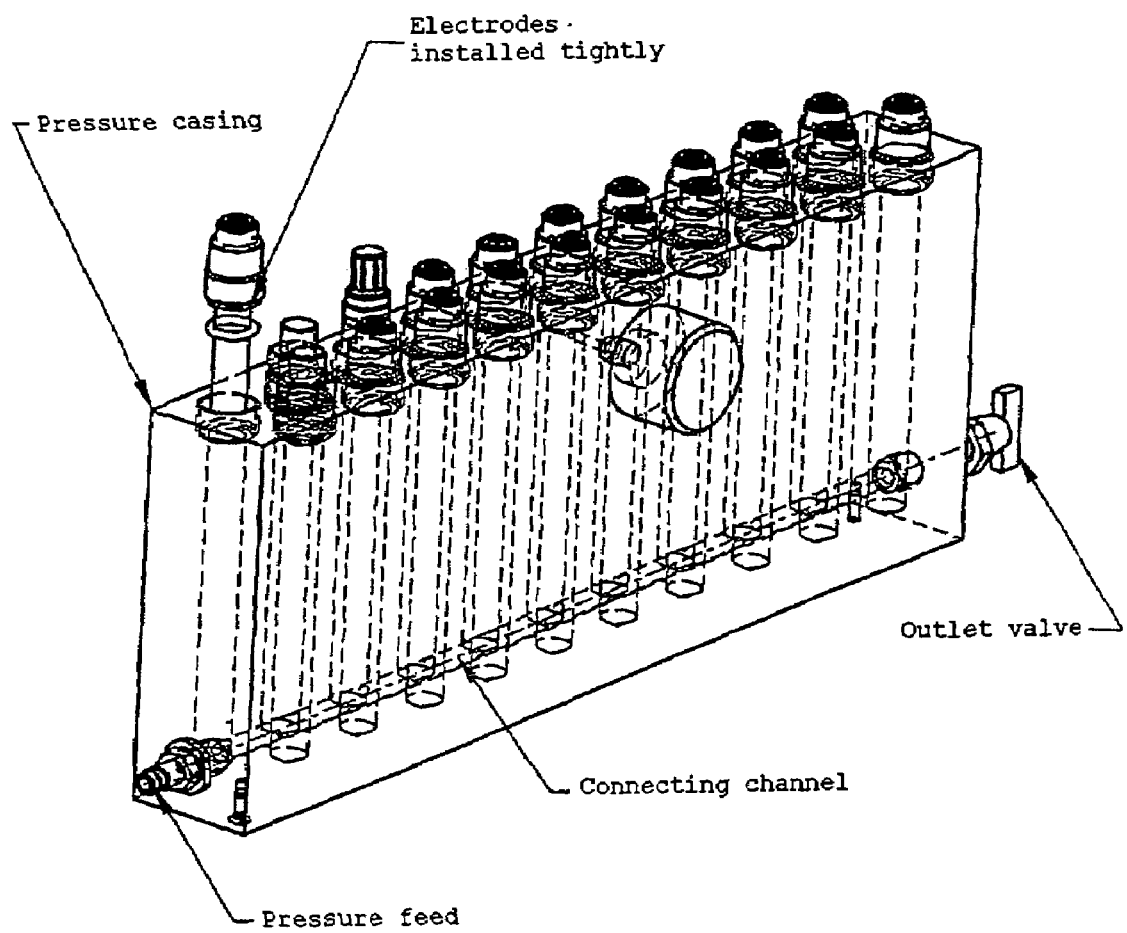

FIG. 2 shows a preferred apparatus for the pressurization of the electrolyte chamber with screwed-in electrodes. Only the diaphragm orifices are exposed to the pressure. The pressure apparatus is sealed via sealing rings between apparatus and inserted electrode heads which protrude to the apparatus.

Figure 3:
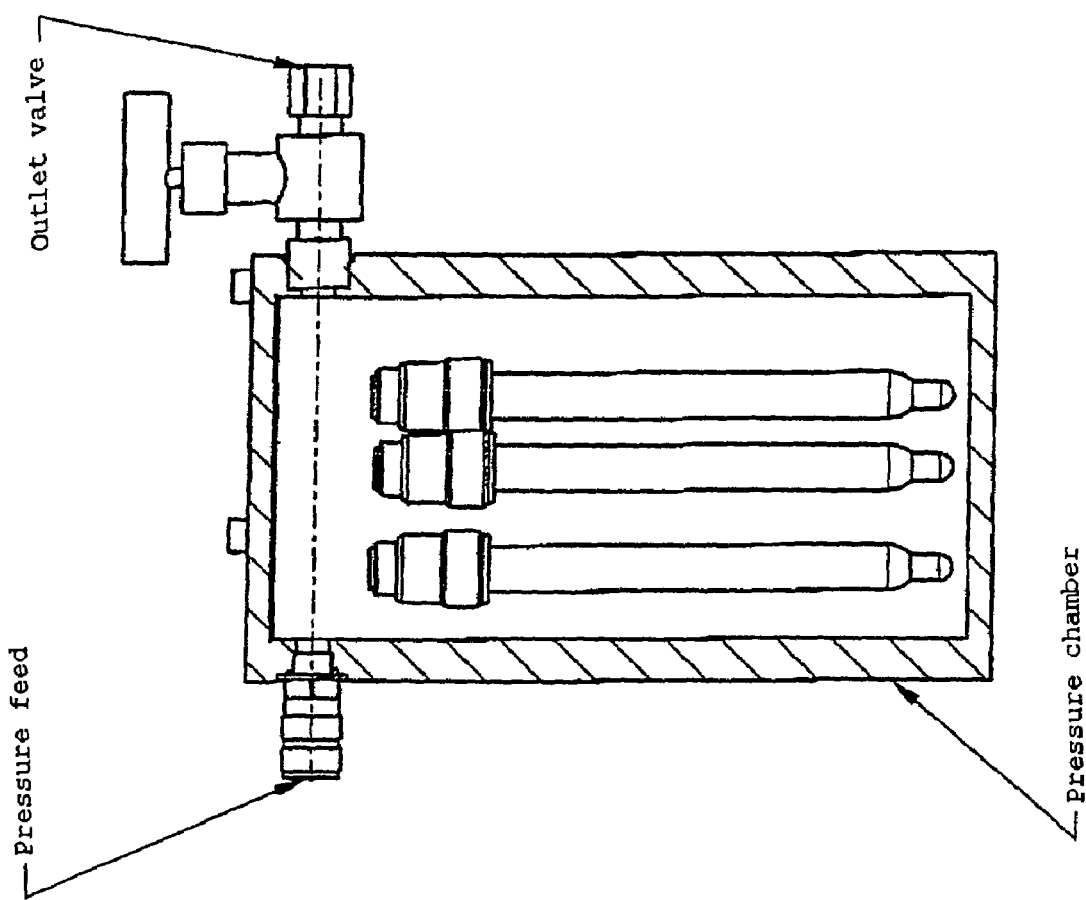

FIG. 3 shows a pressure apparatus into which entire electrodes can be inserted.

EXAMPLES

Example 1

| Porous diaphragm: | silicon dioxide with pore radii of 0.5 µm |
|---|---|
| Electrolyte: | 10% polydimethylacrylamide solution polydimethylacrylamide having a molar weight (weight-average molecular weight) Mw > 500 000 prepared as follows: |

50 g of dimethylacrylamide and 430 g of deionized water and TEMED (tetramethyl) are radically polymerized by adding ammonium persulfate solution. 91.6 g of KCl and 360.5 g of glycerol are added to 450 g of the resulting viscous polymer solution (Mw>500 000; GPC). At elevated temperatures, this electrolyte tends to polymer precipitations. This tendency is enhanced by high salt concentrations. It is possible with 40% glycerol and the above amount of KCl to obtain electrolytes which are stable up to 135° C. Increasing the amount of glycerol or reducing the amount of KCl can further increase the thermal stability. Owing to the lower KCl concentration relative to conventional electrolytes (3 mol/l of KCl), Ag/AgCl reference systems with this electrolyte have a deviation of approx. 8 mV, i.e. the zero point of such an measuring chain in pH 7 buffer is shifted by approx. 8 mV. This can be corrected by appropriately adapting the internal buffer (buffer in the internal discharge system for the ion-sensitive membrane).

Final Composition of the Electrolyte:

| water content | approx. 43% |
|---|---|
| glycerol content | approx. 40% |
| KCl concentration in water | 3.15 mol/l |

Production of the Electrodes:

Filling of the reference chamber with electrolyte, in the course of which a gaseous cavity of 20% of the reference chamber has to be formed. The gaseous cavity is compressible and has the purpose of a compressible space in the event of temperature variations, which prevents hydraulic pressures.

Vertical insertion or screwing in of the electrodes into the pressurization apparatus.

Pressurization of the Electrodes with Nitrogen:

3.5 min at 40 bar overnight at 10 bar

This results in an electrode overpressure of 4 to 6 bar in the reference chamber with an electrolyte out-flow of <0.004 g*bar$^{-1}$*h$^{-1}$.

This electrode is particularly suitable for the monitoring of bioprocesses, in which non-toxic thickeners resistant toward enzymes have to be used. The effluent electrolyte exhibits cleaning action on the diaphragm and minimizes the diaphragm potentials known in biological processes, which can occur as a result of proteins absorbed on the diaphragm.

Example 2

| Porous diaphragm: | zirconium dioxide having pore radii of 8 µm |
|---|---|
| Reference system: | glass membrane in buffered electrolyte pH approx. 4.6 |
| Electrolyte: | acetate-buffered 10% polydimethylacrylamide solution polydimethylacrylamide having a molar weight (weight-average molecular weight) Mw > 800 000 prepared as follows: |

50 g of dimethylacrylamide and 430 g of deionized water and TEMED (tetramethyl) are radically polymerized by adding ammonium persulphate solution. The following are added to 400 g of the resulting viscous polymer solution (Mw>800 000, GPC):

17.4 g of deionized water 275.2 g of glycerol 82.00 g of KCl 30.1 g of sodium acetate 30 g of glacial acetic acid Final Composition of the Electrolyte, pH 4.6:

| water content | approx. 45% |
|---|---|
| glycerol content | approx. 32% |
| KCl concentration in water | approx. 2.81 mol/l |
| acetate concentration in water | approx. 1.88 mol/l |

Production of the Electrodes:

Filling of the reference chamber with electrolyte, in the course of which a gaseous cavity of 20% of the reference chamber has to be formed. The gaseous cavity is compressible and has the purpose of a compressible space in the event of temperature variations, which prevents hydraulic pressures.

Vertical insertion or screwing of the electrodes into the pressurization apparatus.

Pressurization of the Electrodes with Nitrogen:

3.5 min at 40 bar overnight at 10 bar

This results in an elevated electrode pressure of 4 to 6 bar in the reference chamber with an electrolyte out-flow of <0.005 g*bar$^{-1}$*h$^{-1}$.

This electrode is particularly suitable for the monitoring of chemical processes. The reference system is a high-resistance pH reference system which reacts only to pH alteration of the electrolyte. Such electrodes can thus be poisoned in particular by measuring media which have a different pH to the reference electrolyte. The pH of this electrolyte changes only as a result of dilution of the reference electrolyte and the reference signal of the reference electrode thus changes only slightly. In addition, such reference systems are difficult to poison, since they are a pH reference and not a reference of the second type. A disadvantage of such an electrode arrangement is the high reference impedance, which requires the use of special transmitters having correspondingly high-resistance inputs.

In order to obtain an electrode with measuring chain zero point at pH 7 with such an electrolyte, it is necessary to appropriately adjust the internal discharge (glass membrane/ internal electrolyte/Ag/AgCl discharge system) and/or likewise to produce the internal electrolyte with a pH of about 4.6.

Example 3

Analogous to Example 1, with hydroxyethylcellulose-thickened electrolyte system.

Example 4

Analogous to Example 1, 3M KCl electrolyte thickened with 40% glycerol.
Pore radius diaphragm approx. 1 µm
Outflow rate approx. 0.007 g/(bar$^{*-1}$ h)

Example 5

Analogous to Example 1, thickened with polyacrylamide: 100 g of acrylamide, 900 g of deionized water, 223.7 g of KCl and TEMED are radically polymerized by adding ammonium persulphate solution.
Final Concentration of the Electrolyte:

| | |
|---|---|
| Water content | approx. 73% |
| Polymer content | approx. 10% |
| KCl concentration in water | 3.0 mol/l |

10% polyacrylamide solution with 3 mol/l KCl (viscosity 3.5 to 4.5 Pas)
Outflow rate approx. 0.005 g/bar/h.

The invention claimed is:

1. A process for producing a reference electrode comprising:
providing a chamber which has a reference electrolyte, wherein a portion of the wall of said chamber is formed from porous material for contacting said reference electrolyte with a measuring medium and
generating overpressure in said reference electrode by introducing a gas or/and a liquid into said chamber through the porous material of the wall, wherein said gas or/and liquid is in direct contact with the reference electrolyte.

2. Process according to claim 1, characterized in that the permeability of said porous material of the wall of said chamber for the gas and/or liquid introduced to generate the overpressure is higher than for said reference electrolyte.

3. Process according to claim 1, characterized in that said chamber in said reference electrode has a pressure of $\geq 1.1$ bar.

4. Process according to claim 1, said reference electrode comprising a chamber which has a cavity and a reference electrolyte, a portion of the wall of said chamber being formed from porous material for contacting said reference electrode with a measuring medium, and said cavity comprising a gas under pressure, characterized in that
a pressure is generated in said reference electrode by introducing a gas into said cavity through the porous material of the wall of said chamber.

5. Process according to claim 4, characterized in that the gas is present in said cavity at a pressure of $\geq 1.1$ bar.

6. Process for producing a reference electrode, said reference electrode comprising a chamber which has a reference electrolyte, and a portion of the wall of said chamber being formed from porous material for contacting said reference electrolyte with a measuring medium, and said chamber being under overpressure, characterized in that
said reference electrolyte is introduced into said chamber and said chamber is closed under pressure, while said reference electrolyte and said chamber are kept under pressure,
where overpressure is generated by introducing a gas or/and liquid into said chamber through the porous material of the wall, wherein said gas or/and liquid is in direct contact with the reference electrolyte.

7. A reference electrode comprising a chamber under overpressure which contains a reference electrolyte in direct contact with a pressurizing gas or/and liquid, wherein a portion of the wall of said chamber is formed from porous material for contacting said reference electrolyte with a measuring medium,
means for generating overpressure in said reference electrode by introducing a gas or/and liquid into said chamber through the porous material of the wall
wherein said means for generating overpressure comprises said measuring medium and said porous material of the wall and
with the exception of the section of porous material, said reference electrode does not have an orifice and that no further orifice has been provided for the pressurization.

8. Reference electrode according to claim 7, comprising a chamber which has a cavity and a reference electrolyte, a portion of the wall of said chamber being formed from porous material for contacting said reference electrode with a measuring medium, and said cavity comprising gas under pressure.

9. Reference electrode according to claim 8, characterized in that
the gas present in said cavity is oxygen, nitrogen or/and air.

10. Reference electrode according to claim 7, characterized in that
it has a viscous reference electrolyte which comprises as a thickener a linear polymer, in particular a hydrophilic, linear polymer selected from polyacrylates, cellulose derivatives, starch derivatives,dextroses, polyvinyl alcohols, poly (N-vinylpyrrolidones), poly (2-vinylpyridines),polyethylene oxides, polyethylene glycols and derivatives thereof, such as polyethylene glycol monomethyl ethers, polyvinyl acetates, polymaleic acids, polyvinyl methyl ethers, gelatins, agar agar and alginates.

11. Reference electrode according to claim 7, characterized in that
said reference electrode comprises an organic solvent as a thickener, in particular selected from glycerol, ethylene glycol, propylene glycol, diethanolamine, triethanolamine and hydroxylterminal polyethers and/or polyesters.

12. Reference electrode according to claim 7, characterized in that
the porous material of the wall is selected from zirconium oxide or silicon oxide having pore radii in the range of 0.1 to 10 µm.

13. Electrochemical measuring cell, comprising a reference electrode according to claim 7, and a measuring electrode.

* * * * *